(12) United States Patent
Chang et al.

(10) Patent No.: US 10,655,210 B2
(45) Date of Patent: May 19, 2020

(54) ROLL-TO-ROLL SPUTTERING PROCESS WITH HYBRID TARGET AND PRODUCT THEREOF

(71) Applicant: Ace Medical Technology Co., Ltd., Zhubei (TW)

(72) Inventors: Ching-Yu Chang, Taipei (TW); Chien-Fa Liao, Taipei (TW)

(73) Assignee: Ace Medical Technology Co., Ltd., Zhubei (TW)

( * ) Notice: Subject to any disclaimer, the term of this patent is extended or adjusted under 35 U.S.C. 154(b) by 404 days.

(21) Appl. No.: 15/371,841

(22) Filed: Dec. 7, 2016

(65) Prior Publication Data

US 2017/0159165 A1 Jun. 8, 2017

(30) Foreign Application Priority Data

Dec. 8, 2015 (TW) .............................. 104141037 A

(51) Int. Cl.
| | |
|---|---|
| *C23C 14/34* | (2006.01) |
| *C23C 14/20* | (2006.01) |
| *H01J 37/34* | (2006.01) |
| *C23C 14/56* | (2006.01) |
| *C23C 14/04* | (2006.01) |

(Continued)

(52) U.S. Cl.
CPC ............. *C23C 14/205* (2013.01); *A61B 5/00* (2013.01); *A61B 5/14532* (2013.01); *B32B 15/08* (2013.01); *C12Q 1/005* (2013.01); *C12Q 1/006* (2013.01); *C23C 14/042* (2013.01); *C23C 14/14* (2013.01); *C23C 14/3407* (2013.01); *C23C 14/562* (2013.01); *G01N 27/3272* (2013.01); *G01N 33/492* (2013.01); *H01J 37/3277* (2013.01); *H01J 37/34* (2013.01);

(Continued)

(58) Field of Classification Search
CPC .... C23C 14/14; C23C 14/3407; C23C 14/562
See application file for complete search history.

(56) References Cited

U.S. PATENT DOCUMENTS 5,618,388 A * 4/1997 Seeser ........................ C23C 8/02
118/719
7,588,669 B2 * 9/2009 Guo ........................ C23C 14/352
204/298.08

(Continued)

*Primary Examiner* — Jason Berman
(74) *Attorney, Agent, or Firm* — Tracy M. Heims; Apex Juris, pllc.

(57) ABSTRACT

The present invention provides a roll-to roll sputtering process with a hybrid target comprising: unwinding a flexible polymer substrate from an unwinding axis; sputtering a hybrid target to the flexible polymer substrate for forming a first metal film, and a second metal film; and rewinding the flexible polymer substrate to a rewinding axis, and further comprising the following steps of: using laser to form a first electrode section and a second electrode section on the first metal film and the second metal film; and disposing a detecting substance layer on the second electrode section. Moreover, a product made by the roll-to-roll sputtering process is provided. Compared to the prior art, the hybrid target of the present invention is formed by multiple metals and can be sputtered to the substrate for forming multiple metal thin films. The present invention has an advantage of shortening the processing time and saving cost.

8 Claims, 6 Drawing Sheets

(51) Int. Cl.
  *A61B 5/00*  (2006.01)
  *H01J 37/32*  (2006.01)
  *B32B 15/08*  (2006.01)
  *A61B 5/145*  (2006.01)
  *C23C 14/14*  (2006.01)
  *C12Q 1/00*  (2006.01)
  *G01N 27/327*  (2006.01)
  *G01N 33/49*  (2006.01)

(52) U.S. Cl.
  CPC ... H01J 37/3429 (2013.01); *A61B 2562/0295* (2013.01); *A61B 2562/12* (2013.01)

(56) References Cited

U.S. PATENT DOCUMENTS

| | | | |
|---|---|---|---|
| 2006/0088945 A1* | 4/2006 | Douglas | C12Q 1/001 436/518 |
| 2010/0089621 A1 | 4/2010 | Stoss et al. | |
| 2014/0308459 A1* | 10/2014 | Miyazaki | C12Q 1/001 427/555 |

* cited by examiner

FIG. 1(A)
FIG. 1(B)
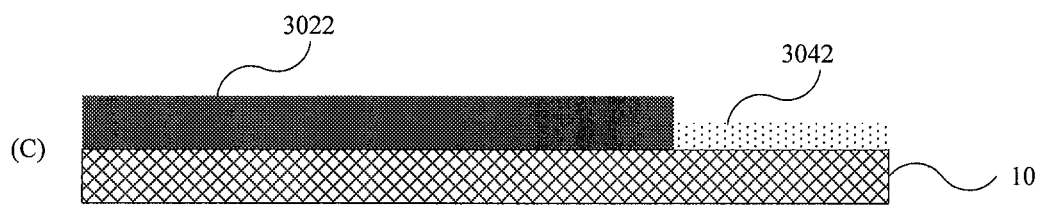
FIG. 1(C)
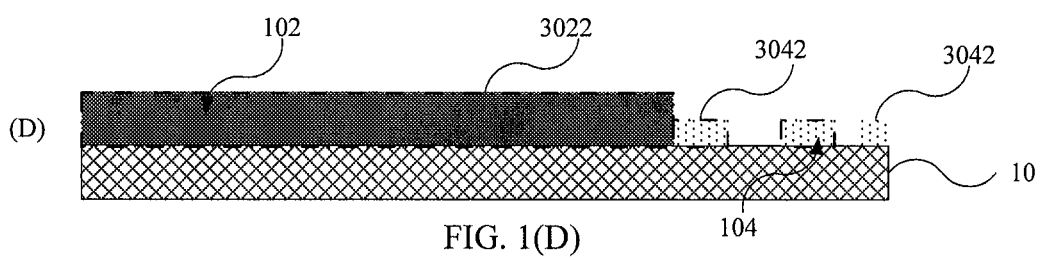
FIG. 1(D)
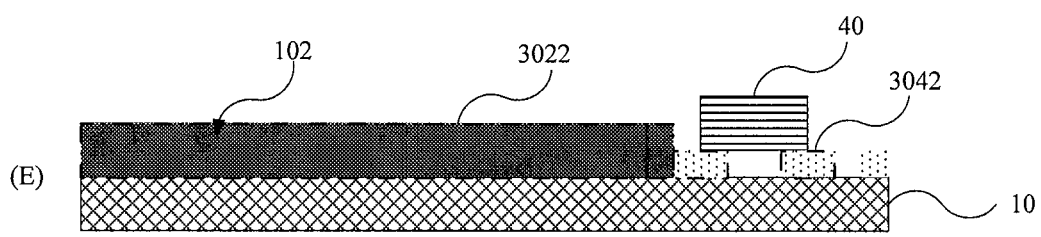
FIG. 1(E)
FIG. 1

2
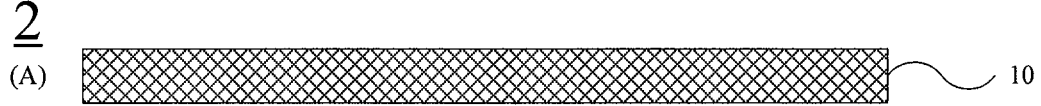
FIG. 1(A)
FIG. 1(B)
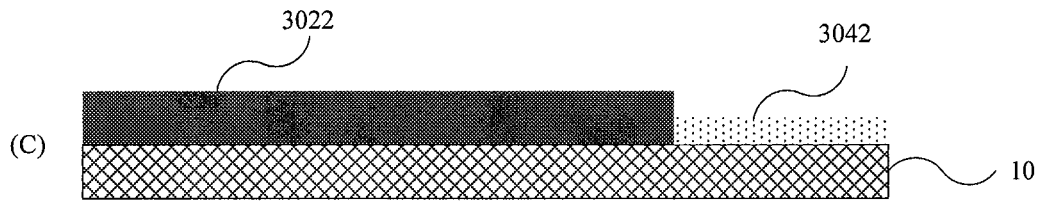
FIG. 1(C)
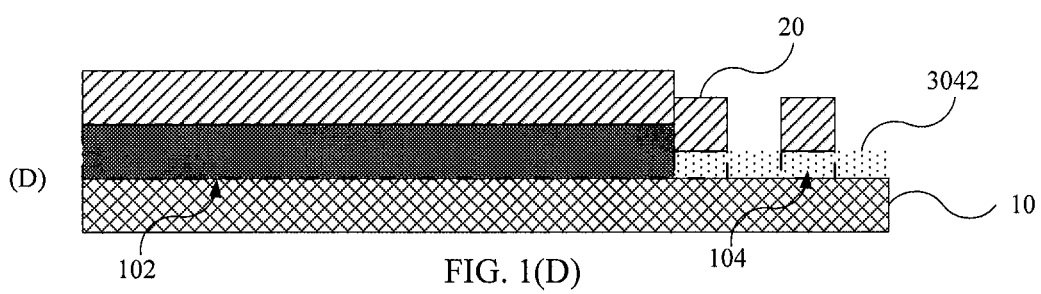
FIG. 1(D)
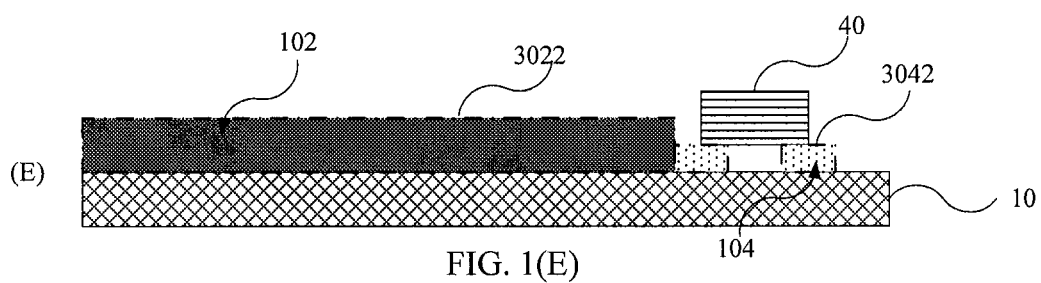
FIG. 1(E)
FIG. 5

ROLL-TO-ROLL SPUTTERING PROCESS WITH HYBRID TARGET AND PRODUCT THEREOF

BACKGROUND OF THE INVENTION

1. Reference to Related Applications

This application claims the right of priority based on TW application Serial No. 104141037, filed on Dec. 8, 2015, and the content of which is hereby incorporated by reference in its entirety.

2. Field of the Invention

The present invention relates to a roll-to-roll sputtering process with a hybrid target and a product thereof, and more particularly, to a roll-to-roll sputtering process with a hybrid target and a product thereof using the hybrid target formed by a variety of metals sequentially to process sputtering and produce products.

3. Description of the Prior Art

In the prior art, the process of roll-to-roll is unwinding raw flexible material through an unwinding axis from a cylindrical retracting flexible material to be processed, through processing operations, such as, precision stamping, laminating, coating, printing and other processing operations, and then the flexible material completed processing is rewinded through the rewinding axis. Due to the convenience of rewinding and unwinding raw material and finished product, it is considered as a high performance and low cost continuous production mode, which is even popular with the flexible electronic product manufacturing industry.

Taking coating as an example; a coating process during unwinding-rewinding process can be used to produce flexible transparent conductive film such as ITO film used in touch panels or the electrodes used in blood glucose test strip. When producing a multilayer flexible transparent conductive film, each layer of the conductive film is sputtered on almost the entire surface of the flexible material separately. Several repeated coating operations are needed for all layers in order to complete the coating process.

However, when producing the blood glucose test strips, each piece of blood glucose test strips needs to have at least one pair of electrodes (such as working and counter electrodes) and extending conductive wires of the electrodes (extending electrode) at the same time, and the area occupied by each electrode varies. Basically, because the metal used for working electrode and counter electrode should be very stable and chemical inert, precious metal such as gold, platinum or palladium normally is used for producing the working and counter electrodes. Precious metal is very expensive compared to normal metal or current mostly used carbon electrode. However, normal metal such as copper or its alloy with good electric conductive property is good to be used for the extending electrode with low cost. If using the conventional sputtering process of producing flexible transparent conductive film to produce the blood glucose test strips, precious metal should be used for the entire strip on both the working electrode and the extending electrode area due to the electrode stability requirement. Considering of the cost, the entire precious metal strip is lack of competition ability in the blood glucose test strip market. An idea for reducing the cost and still keeping the stability of the test strip's electrodes is to coat the precious metal on the working electrode and the normal metal on the extending electrode separately. However, the difficulty to use the conventional sputtering process to produce such kind of blood glucose test strips is that it needs to have different metal precisely positioned on the working and extending electrode in several coating operations. In other words, the different metal for the working electrode and the extending electrode needs to be coated precisely on different partial surface of the entire flexible material by several coating processes first, and then to remove the unnecessary portion of the metal film. This process may not only increase the complexity of the processes but also result in overlapping, and there may be mutual interference between each coating operation.

In conclusion, a process that can complete all coating operations in one time to avoid the overlapping and mutual interference is needed to reduce the time and the cost of manufacturing.

SUMMARY OF THE INVENTION

In response to the above-mentioned problems, an object of the present invention is to provide a roll-to-roll sputtering process with a hybrid target that can simultaneously sputter a plurality of metal films to a flexible substrate, comprising the following steps of: unwinding a flexible polymer substrate from an unwinding axis; sputtering the hybrid target to the flexible polymer substrate for forming a first metal film and a second metal film; and rewinding the flexible polymer substrate to a rewinding axis.

Wherein, the hybrid target comprises a first metal and a second metal, and the first metal and the second metal are connected to each other to form the hybrid target.

Wherein, the process can further comprise the following steps of: using laser to form a first electrode (such as extending electrode) section on the second metal film and a second electrode (such as working electrode) section on the first metal film; and disposing a detecting substance layer on the second electrode section.

Wherein, the first metal can be a precious metal and the second metal can be a normal metal, and the first metal film can be a precious metal film and the second metal film can be a normal metal film.

Another object of the present invention is to provide a roll-to-roll sputtering process with a hybrid target that can simultaneously sputter a plurality of metal films to a flexible substrate, comprising the following steps of: unwinding a flexible polymer substrate from an unwinding axis; sputtering the hybrid target to the flexible polymer substrate for forming a first metal film and a second metal film; covering a blocked layer on the first metal film and the second metal film for defining the patterns of a first electrode section and a second electrode section; removing the unblocked metal film; removing the blocked layer; disposing a detecting substance layer on the second electrode section; and rewinding the flexible polymer substrate to a rewinding axis;

Another object of the present invention is to provide a product produced by a roll-to-roll sputtering process with a hybrid target, wherein the hybrid target comprises a first metal and a second metal, comprising: a flexible polymer substrate and a first electrode section and a second electrode section are defined on the flexible polymer substrate; a first metal film disposed on the second electrode section; a second metal film disposed on the first electrode section; and a detecting substance layer disposed on the second electrode section.

Wherein the first metal film and the second metal film are formed by the first metal and the second metal of the hybrid target sputtered on the flexible polymer substrate.

Compared to the prior art, the present invention uses the hybrid target formed by a variety of metals sequentially to process sputtering and can form a plurality of metal films to the flexible substrate simultaneously to avoid the overlapping and mutual interference. The present invention can shorten the processing time and the processing procedures to save cost, and furthermore, improve the accuracy of the use of the product via the good electrical and mechanical properties of the precious metal.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein:

FIG. 1(A) to FIG. 1(E) show a schematic diagram of the process stages respectively in an embodiment of the present invention.

FIG. 3 shows a top view diagram of the product produced by the process in an embodiment of the present invention, wherein FIG. 1(A) to FIG. 1(E) are cross-section diagrams crossing along to the I-I line in FIG. 3.

Figure 4:
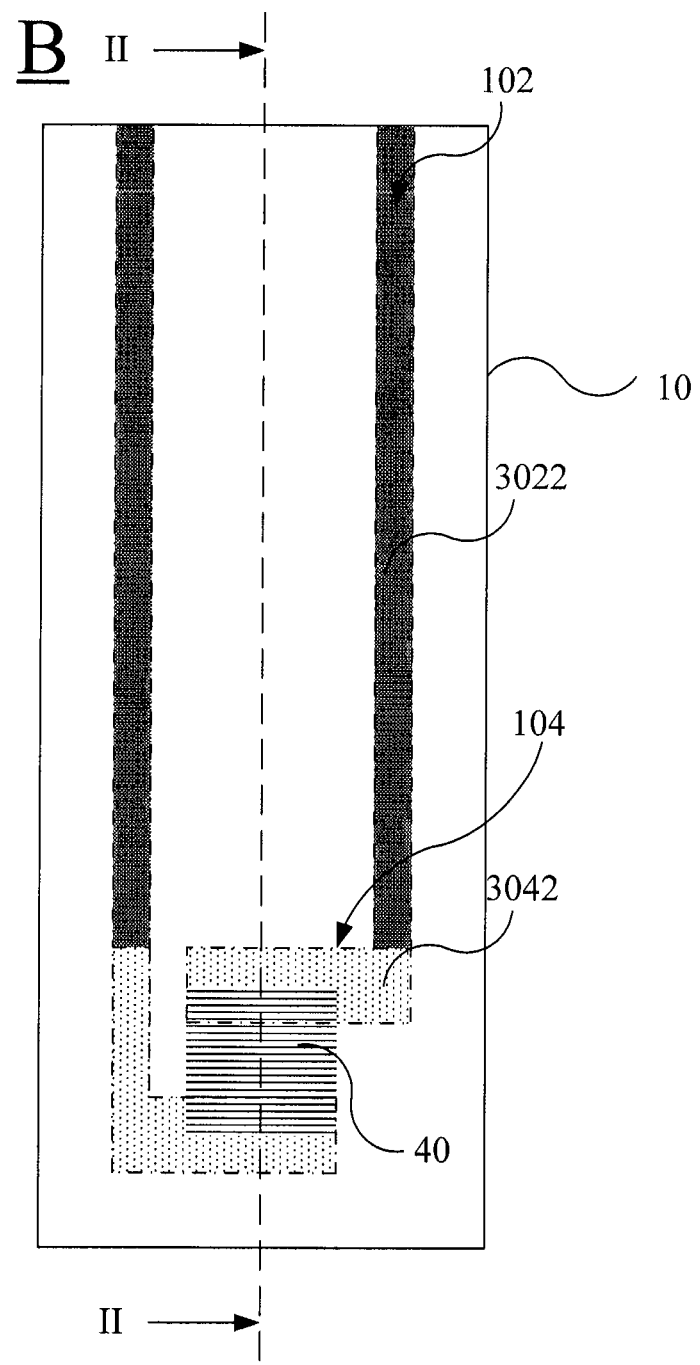
FIG. 4 shows a top view diagram of the product produced by the process in another embodiment of the present invention.

FIG. 5(A) to FIG. 5(E) show a schematic diagram of the process stages respectively in another embodiment of the present invention, wherein FIG. 5(A) to FIG. 5(E) are cross-section diagrams crossing along to the II-II line in FIG. 4.

FIG. 6(A) to FIG. 6(E) show a schematic diagram of the process stages respectively in another embodiment of the present invention, wherein FIG. 6(A) to FIG. 6(E) are cross-section diagrams crossing along to the II-II line in FIG. 4.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 2:
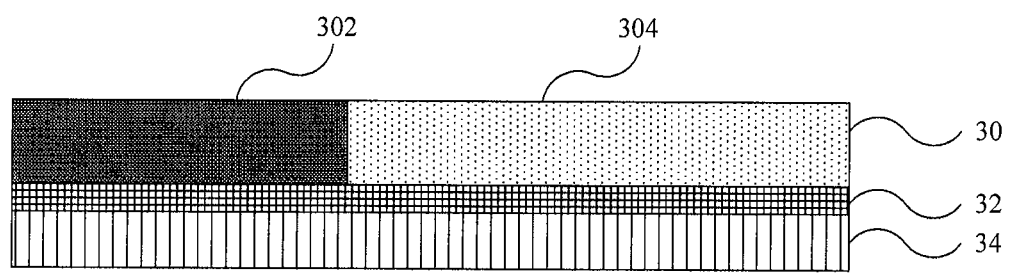
FIG. 2 shows a cross-section diagram of the hybrid target of the present invention.

First, please refer to FIG. 1 and FIG. 2. FIG. 1 (A) to (E) show a schematic diagram of the process stages respectively in an embodiment of the present invention. FIG. 2 shows a cross-section diagram of the hybrid target of the present invention. The present invention provides a roll-to-roll sputtering process 1 with a hybrid target (hereafter referred to as process 1) that can sputter a plurality of metal films to the flexible substrate simultaneously, comprising the following steps of: S1: unwinding a flexible polymer substrate from an unwinding axis (not shown); S2: sputtering the hybrid target to the flexible polymer substrate for forming a first metal film and a second metal film; and S3: rewinding the flexible polymer substrate completed processing to a rewinding axis.

Wherein, the process can further comprise the following steps of: S4: using laser to form a first electrode section and a second electrode section; and S5: disposing a detecting substance layer on the second electrode section.

Wherein, the steps of S4 and S5 can be operated on a machine that is different from the machine that processes the steps of S1, S2 and S3.

The following will describe the detail of the process steps of the present invention. The embodiment of the present invention takes the test strip used in the glucose test devices for example. First execute step S1: unwinding a flexible polymer substrate from an unwinding axis. Wherein the flexible polymer substrate 10 shown in FIG. 1(A) comprises, but not limited to, one of Polyethylene Terephthalate (PET) or Polycarbonate (PC) or the composition thereof.

Next execute step S2: sputtering the hybrid target to the flexible polymer substrate for forming a first metal film and a second metal film. The hybrid target 30 shown in FIG. 1(B) is sputtered to the flexible polymer substrate 10 for forming the first metal film 3042 and the second metal film 3022. As FIG. 1(C) shown, wherein the hybrid target 30 comprises the first metal 304 and the second metal 302, and the first metal 304 and the second metal 302 are connected to each other to form the hybrid target 30. Step S2 is to form the first metal film 3042 and the second metal film 3022 respectively through the sputtering process that sputters the first metal 304 and the second metal 302 to the surface of the flexible polymer substrate 10.

The connective way of the hybrid target 30 is shown in FIG. 2. FIG, 2 and FIG. 1(B) are the cross-section diagram and the front view diagram of the hybrid target 30 respectively. Wherein, the hybrid target 30 comprises a metal plate 34, a cement 32, a first metal 304 and a second metal 302. Take the rectangular hybrid target 30 in the embodiment of the present invention for example, the hybrid target 30 uses copper (Cu) as the metal plate 34, and indium (In) is disposed on the metal plate 34 as the cement 32, and then the first metal 304 and the second metal 302 are disposed on the cement 32 for forming the hybrid target 30. However, the material of the metal plate 34 is not limited to copper, and it can also be stainless steel or titanium. Besides, the shape of the hybrid target 30 is not only rectangular, but also cylindrical, so that the user can choose to use the rectangular hybrid target 30 or the cylindrical hybrid target 30 according to the needs of the process of the present invention.

According to the connective way of the hybrid target 30 as above-mentioned, the roll-to-roll sputtering process 1 with the hybrid target of the present invention further comprises step S0: preparing a hybrid target. The hybrid target 30 is prepared from the metal plate 34, the cement 32, the first metal 304 and the second metal 302 according to the above-mentioned way.

Wherein, the first metal 304 includes gold, palladium, silver, indium (In) and other conventional precious metal and alloys or oxides like ITO thereof; and the second metal 302 can be copper and nickel and other conventional normal metal and their alloys thereof. The disposing way of the first metal 304 and the second metal 302 on the hybrid target 30 is arranged according to the patterns of the second electrode section 104 and the first electrode section 102 on the blood glucose test strip of the user. An intermediary material (not shown) needs to be added between the first metal 304 and the second metal 302 for segmentation if necessary.

Or in another embodiment of the present invention, the sputtering process of step S2 can be processed sequentially to sputter the first metal 304 and the second metal 302 to the flexible polymer substrate 10. For example, a mask is set between the hybrid target 30 and the flexible polymer substrate 10, and the mask shields the area of the flexible polymer substrate 10 to be sputtered with the second metal 302 and reveals the area to be sputtered with the first metal 304. Then process sputtering, and only the area to be sputtered with the first metal 304 is sputtered to form the first metal film 3042. The mask is swapped to shield the area of the flexible polymer substrate 10 to be sputtered with the first metal 304, and then the second metal 302 is sputtered on the area to be sputtered with the second metal 302 to form the second metal film 3022. The above-mentioned shielding sequence can be changed freely, and be used in the aftermentioned process of the present invention.

Next process step S3: rewinding the flexible polymer substrate to a rewinding axis (not shown) to complete the roll-to-roll sputtering process 1 with the hybrid target of the present invention.

Figure 3:
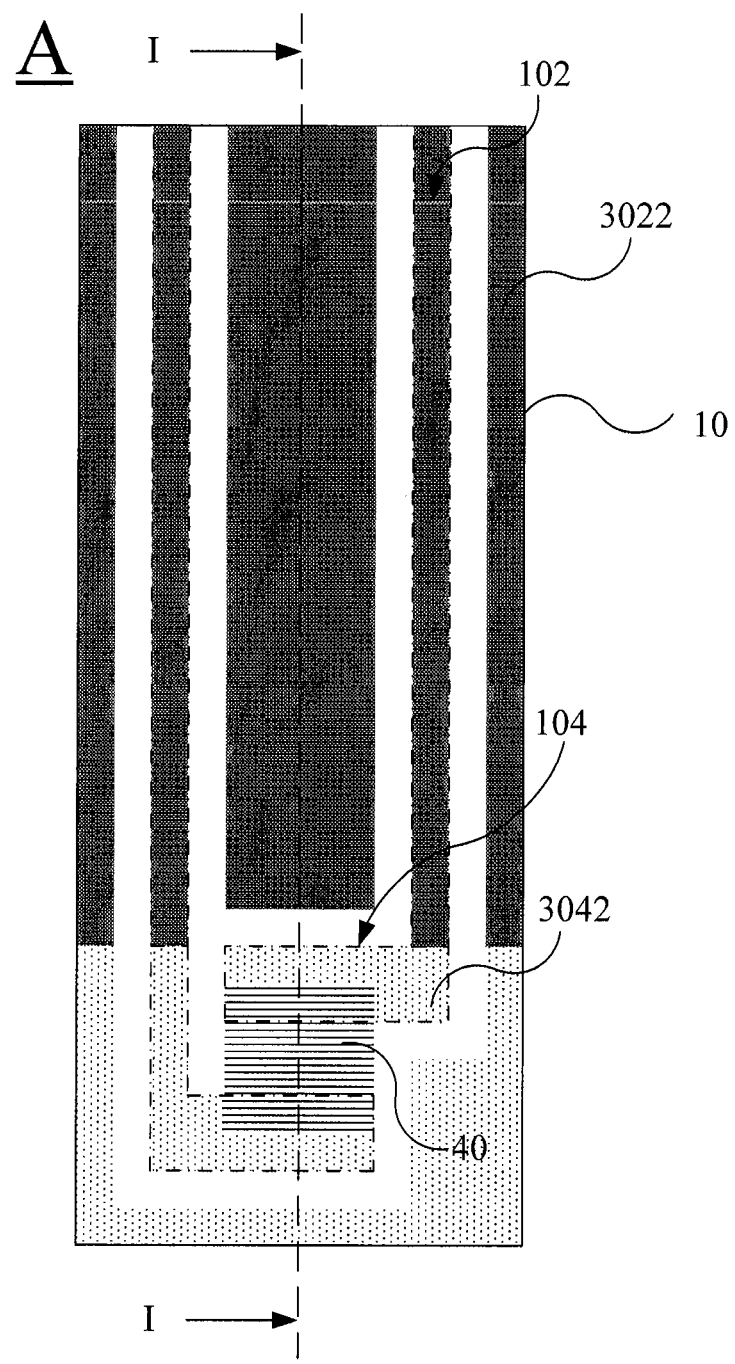

Please refer to FIG. 1 and FIG. 3 at the same time. FIG. 3 shows a top view diagram of the product produced by the process in an embodiment of the present invention, wherein FIG. 1(A) to FIG. 1(E) are cross-section diagrams crossing along the I-I line in FIG. 3. Then process step S4: using laser to form the first electrode section 102 and the second electrode section 104 on the second metal film 3022 and the first metal film 3042 respectively. As mentioned above, the disposing way of the first metal 304 and the second metal 302 on the hybrid target 30 is arranged according to the patterns of the first electrode section 102 and the second electrode section 104 on the blood glucose test strip of the user. In this step, the user can operate the instrument to use laser to cut the outline of the first electrode section 102 on the second metal film 3022 and the second electrode section 104 on the first metal film 3042 respectively. The first electrode section 102 and the second electrode section 104 are shown as the dot line block in FIG. 3, FIG. 1(D) and FIG. 1(E).

Finally process step S5: disposing a detecting substance layer on the second electrode section 104. In the embodiment of the present invention, the second electrode section 104 is one end that contacts with the biochemical specimen, and the detecting substance layer 40 comprises the conventional biochemical substance that is needed when detecting the blood glucose; however, the present invention is not limited to, and the user can dispose suitable detecting substance or do not dispose detecting substance according to the manufacturing requirements. For example, the detecting substance layer 40 comprises enzyme, electron transfer intermediate, buffer solution and thickener, and is disposed on the second electrode section 104 for detecting blood glucose, uric acid and hemoglobin. While not disposing the detecting substance layer 40, taking detecting DNA as an example, whether the test sample contains DNA to be detected is interpreted by detecting the electrical change detected by the second electrode section 104.

It is important to note that whether the material of the hybrid target 30 reacts with the detecting substance layer 40 or not. For example, as mentioned above, the material composition of the hybrid target 30 needs to add the intermediary material between the first metal 304 and the second metal 302 to be in coordination with the disposition of the second electrode section 104 and the first electrode section 102. It should be noted whether the intermediary material reacts with the detecting substance layer 40 at this time or not, in order to avoid the product cannot successfully perform the functions.

Please refer to FIG. 4 and FIG. 5. FIG. 4 shows a top view diagram of the product produced by the process in another embodiment of the present invention. FIG. 5(A) to FIG. 5(E) show a schematic diagram of the process stages respectively in another embodiment of the present invention, wherein FIG. 5(A) to FIG. 5(E) are cross-section diagrams crossing along to the II-II line in FIG. 4. The present invention further provides a roll-to-roll sputtering process 2 with a hybrid target (hereafter referred to as process 2) that can sputter a plurality of metal films to the flexible substrate simultaneously, comprising the following steps of: C1: unwinding a flexible polymer substrate from an unwinding axis (not shown); C2: sputtering the hybrid target to the flexible polymer substrate for forming a first metal film and a second metal film; C3: covering a blocked layer on the first metal film and the second metal film for defining the patterns of a first electrode section and a second electrode section; C4: removing the metal film on the unblocked area and then remove the blocked layer; C5: disposing a detecting substance layer on the second electrode section; and C6: rewinding the flexible polymer substrate completed processing to a rewinding axis.

Wherein, the embodiment of the present invention also takes the test strip used in the glucose test device for example. Step C1 and step C2 of process 2 are the same as step S1 and step S2 of process 1, and also further comprises step C0: preparing a hybrid target. The difference is that after step C3, process 2 is to cover a blocked layer 20 on the first metal film 3042 and the second metal film 3022 for defining the patterns of the second electrode section 104 and the first electrode section 102. As shown in the position marked by the dot line block in FIG. 5(D), FIG. 5(E) and FIG. 4. The blocked layer 20 is formed on the flexible polymer substrate 10 through screen printing, applying photoresist film or photolithography.

Or maybe the blocked layer 20 can be a kind of plastic film. In the present invention, the user can cut out some space of the plastic film in order to be in coordination with the shape of the first electrode section 102 and the second electrode section 104, and then dispose the plastic film to the flexible polymer substrate 10 as the blocked layer 20; or dispose the plastic film to the flexible polymer substrate 10 as the blocked layer 20 directly and then cut out some space of the plastic film in order to be in coordination with the shape of the first electrode section 102 and the second electrode section 104.

Next execute step C4: removing the metal film on the unblocked area and the blocked layer. As FIG. 5(E) shown, the first metal film 3042 and the second metal film 3022 that are not covered with the blocked layer 20 are removed through etching process or sandblasting process, and then remove the blocked layer. Only the second electrode section 104 and the first electrode section 102 are remained after C4 completed. And then execute step C5: disposing a detecting substance layer on the second electrode section. In the embodiment of the present invention, the second electrode section 104 is one end that contacts with the biochemical specimen, the detecting substance layer 40 is disposed on the second electrode section 104, and the detecting substance layer 40 comprises the conventional biochemical substance that is needed when detecting the blood glucose. However, the present invention is not limited to the above described material, and the user can dispose suitable detecting substance or do not dispose detecting substance according to the manufacturing requirements. For example, when detecting DNA, whether the test sample contains DNA to be detected is interpreted by detecting the electrical change of the second electrode section 104.

Finally process step C6: rewinding the flexible polymer substrate to a rewinding axis to complete the whole process. The finished product after the process is completed is shown as FIG. 4.

Furthermore, C6 can be performed earlier just after step C2 or C4 and leave other steps, C3, C4 and C5 or C5 to be performed by other machine or performed piece by piece.

Figure 6:
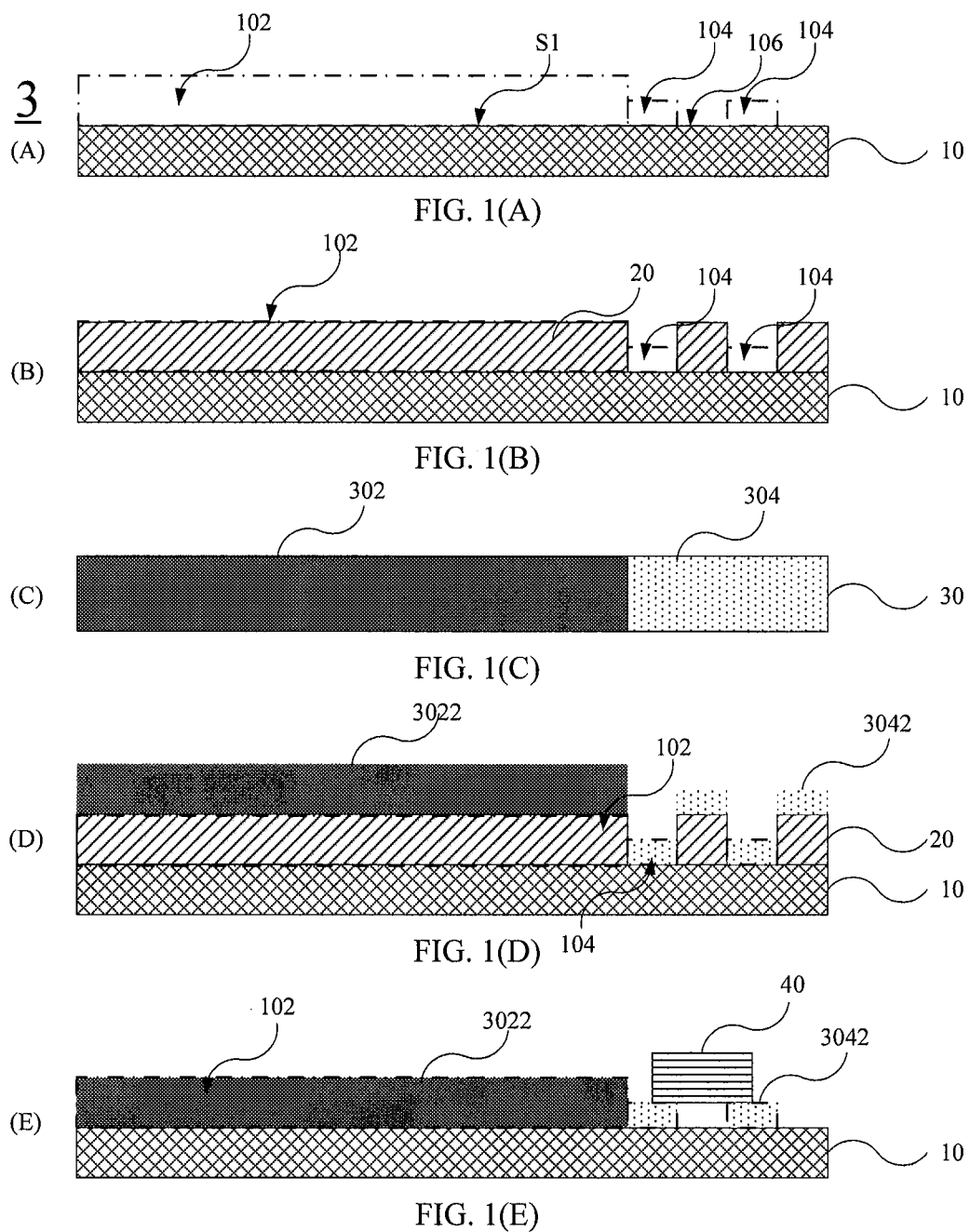

Lastly, please refer to FIG. 4 and FIG. 6. FIG. 6(A) to FIG. 6(E) show a schematic diagram of the process stages respectively in another embodiment of the present invention, wherein FIG. 6(A) to FIG. 6(E) are cross-section diagrams crossing along to the II-II line in FIG. 4. The present invention further provides a roll-to-roll sputtering process 3 with a hybrid target (hereafter referred to as process 3) that can sputter a plurality of metal films to the flexible substrate simultaneously, comprising the following steps of: D1: unwinding a flexible polymer substrate from an unwinding axis (not shown), wherein the flexible polymer substrate comprises a first surface, and the first surface is configured with a first electrode section, a second electrode section and a blank space; D2: disposing a blocked layer on the blank space of the flexible polymer substrate; D3: sputtering a hybrid target to the flexible polymer substrate and the blocked layer; D4: removing the blocked layer; D5: disposing a detecting substance layer on the second electrode section; and D6: rewinding the flexible polymer substrate completed processing to a rewinding axis (not shown).

Wherein, the embodiment of the present invention takes the test strip used in the glucose test device for example. As shown in FIG. 1(A), in step D1: the flexible polymer substrate 10 comprises, but not limited to, one of Polyethylene Terephthalate (PET), Polycarbonate (PC) or the composition thereof.

Next execute step D2: disposing a blocked layer on the blank space of the flexible polymer substrate. As FIG. 6(B) shown, the blocked layer 20 is formed on the flexible polymer substrate 10 through screen printing, applying photoresist film or photolithography. It should be noticed that according to the II-II line in FIG. 4, the first electrode section 102 in FIG. 6(B) is located behind the blocked layer, not be filled in the blocked layer. Or maybe the blocked layer 20 can be a kind of plastic film. In the present invention, the user can cut out some space of plastic film in order to be in coordination with the shape of the first electrode section 102 and the second electrode section 104 and then dispose the plastic film to the flexible polymer substrate 10 as the blocked layer 20, so that in the following step the second metal 302 and the first metal 304 can be sputtered to the flexible polymer substrate 10; or dispose the plastic film to the flexible polymer substrate 10 as the blocked layer 20 directly and then cut out some space of the plastic film in order to be in coordination with the shape of the first electrode section 102 and the second electrode section 104 and then to process the following sputtering process.

Next execute step D3: sputtering a hybrid target to the flexible polymer substrate and the blocked layer to form a first metal film and a second metal film. In this step, the hybrid target 30 shown in FIG. 6(C) is disposed on the flexible polymer substrate 10 through sputtering, wherein the hybrid target 30 comprises the first metal 304 and the second metal 302. The connective way and configuration way are as suggested in the previous paragraph, so they will not be repeated here again. In step D3, the second metal 302 is sputtered to the flexible polymer substrate 10 and the blocked layer for forming the second metal film 3022 which partly is filled into the first electrode section 102; the first metal 304 is sputtered to the flexible polymer substrate 10 and the blocked layer for forming the first metal film 3042 which partly is filled into the second electrode section 104, as FIG. 6(D) shown.

In the embodiment of the present invention, the hybrid target 30 is sputtered to the flexible polymer substrate 10 directly, so that the blocked layer 20 is also sputtered with a layer of metal film. The present invention further comprises a step to set a mask between the hybrid target 30 and the flexible polymer substrate 10 to avoid the composition of the metal film of each electrode zone been affected when the hybrid target 30 is sputtered to the flexible polymer substrate 10. For example, in the embodiment of the present invention, in step D3, the above-mentioned mask is not set, so that part of the second metal 302 may be sputtered into the second electrode section 104, and cause the first metal film 3042 of the second electrode section 104 to mix with the second metal 302, and then the accuracy of measurement would be affected in the future.

After finish step D3, use etching process or sandblasting process to execute step D4: removing the blocked layer, to remove the blocked layer 20 and remain the second electrode section 104 formed by the first metal film 3042 and the first electrode section 102 formed by the second metal film 3022. Next execute step D5: disposing the detecting substance layer 40 on the second electrode section 104, as FIG. 6(E) shown.

Finally execute step D6: rewinding the flexible polymer substrate completed processing to a rewinding axis to complete the whole process. The finished product after the process is completed is shown as FIG. 4.

Furthermore, D6 can be performed earlier just after step D3 or D4 and leave other steps, D4 and D5 or D5 to be performed by other machine or performed piece by piece.

The above-mentioned introduces the roll-to-roll sputtering process with the hybrid target of the present invention. While another object of the present invention is to provide a product A (hereafter referred to as embodiment A) produced by the roll-to-roll sputtering process with the hybrid target for producing blood glucose test strip, wherein the hybrid target 30 comprises a first metal 304 and a second metal 302. The product A comprises a flexible polymer substrate 10, a first electrode section 102, a second electrode section 104, a first metal film 3042, a second metal film 3022 and a detecting substance layer 40, as FIG. 3 shown.

Wherein the first metal film 3042 and the second metal film 3022 is formed on the surface of the flexible polymer substrate 10 through sputtering the hybrid target 30, and the first electrode section 102 and the second electrode section 104 are formed on the second metal film 3022 and the first metal film 3042 respectively through laser cutting process, etching process or sandblasting process, and the detecting substance layer 40 is disposed on the second electrode section 104.

The product A produced by the roll-to-roll sputtering process with the hybrid target further comprises an embodiment B (hereafter referred to as embodiment B), and the composition of embodiment B is totally the same as embodiment A. Wherein, process 1 described in the above paragraph of the specification can be used to produce embodiment A; while process 2 and process 3 can be used to produce embodiment B, as FIG. 3 and FIG. 4 shown.

When embodiment A or embodiment B is used as a blood glucose test strip, a specimen to be detected is placed on the detecting substance layer 40, and then embodiment A or embodiment B is put into a blood glucose test device. The blood glucose test device receives from the first electrode section 102 the electrical change which is detected by the second electrode section 104 to detect the blood glucose of the specimen.

In conclusion, the present invention provides the roll-to-roll sputtering process with the hybrid target comprising: forming a hybrid target by the connection of the first metal and the second metal, sputtering the hybrid target to the flexible polymer substrate for forming the first metal film and the second metal film simultaneously, using laser to remove part of the first metal film and the second metal film for forming the first electrode section and the second electrode section, and then disposing the detecting substance to the second electrode section to complete the roll-to-roll sputtering process of the present invention. The present invention further provides the product generated by the roll-to-roll sputtering process with the hybrid target, and the first metal and the second metal are sputtered to the flexible polymer substrate through the above-mentioned process.

Compared to the prior art, the present invention uses the hybrid target formed by a variety of metals sequentially to process sputtering, and can form a plurality of metal films to the flexible substrate simultaneously to avoid the overlapping and mutual interference. The present invention can shorten processing time and processing procedure to save cost, and furthermore, improve the accuracy of the use of the product via the good electrical and mechanical properties of the precious metal.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A roll-to-roll sputtering process with a hybrid target, comprising the following steps of:
   unwinding a flexible polymer substrate from an unwinding axis;
   providing the hybrid target which comprises a first metal and a second metal, and covering an area of the flexible polymer substrate, which is about to be plated with either the first metal or the second metal, with a mask, and sputtering either the first metal or the second metal on another area of the flexible polymer substrate which is not covered by the mask, and then covering the another area of the flexible polymer substrate which is plated with either the first metal or the second metal, and sputtering the other metal on the area of the flexible polymer substrate which has not been plated with either the first metal or the second metal, thereby to sequentially sputter the hybrid target to the flexible polymer substrate for forming a first metal film and a second metal film at different points in time, wherein the first metal and the second metal are connected to each other to form the hybrid target, and the first metal film and the second metal film are adjacently and directly formed on a surface of the flexible polymer substrate;
   patterning the first metal film and the second metal film to respectively form a second electrode section and a first electrode section; and
   rewinding the flexible polymer substrate with the second electrode section and the first electrode section to a rewinding axis;
   wherein the first electrode section is electrically connected to the second electrode section to form a test strip, and the first metal film is a precious metal film and the second metal film is a normal metal film.

2. The roll-to-roll sputtering process with the hybrid target of claim 1, wherein the process further comprises the following steps of:
   using laser to form the first electrode section and the second electrode section on the first metal film and the second metal film; and
   disposing a detecting substance layer on the second electrode section.

3. The roll-to-roll sputtering process with the hybrid target of claim 1, wherein the first metal is a precious metal and the second metal is a normal metal.

4. The roll-to-roll sputtering process with the hybrid target of claim 1, further comprising the step of preprocessing the hybrid target.

5. The roll-to-roll sputtering process with the hybrid target of claim 1, wherein the flexible polymer substrate comprises one of Polyethylene Terephthalate (PET) or Polycarbonate (PC) or the composition.

6. A roll-to-roll sputtering process with a hybrid target, comprising the following steps of:
   unwinding a flexible polymer substrate from an unwinding axis;
   providing the hybrid target which comprises a first metal and a second metal, and covering an area of the flexible polymer substrate, which is about to be plated with either the first metal or the second metal, with a mask, and sputtering either the first metal or the second metal on another area of the flexible polymer substrate which is not covered by the mask, and then covering the another area of the flexible polymer substrate which is plated with either the first metal or the second metal, and sputtering the other metal on the area of the flexible polymer substrate which has not been plated with either the first metal or the second metal, thereby to sequentially sputter the hybrid target to the flexible polymer substrate for forming a first metal film and a second metal film at different points in time, wherein the first metal and the second metal are connected to each other to form the hybrid target, and the first metal film and the second metal film are adjacently and directly formed on a surface of the flexible polymer substrate;
   patterning the first metal film and the second metal film to respectively form a second electrode section and a first electrode section;
   covering a blocked layer on the first metal film and the second metal film for defining the patterns of the first electrode section and the second electrode section;
   removing the metal film on the unblocked area and the blocked layer;
   disposing a detecting substance layer on the second electrode section; and
   rewinding the flexible polymer substrate with the second electrode section and the first electrode section to a rewinding axis;
   wherein the first electrode section is electrically connected to the second electrode section to form a test strip, and the first metal film is a precious metal film and the second metal film is a normal metal film.

7. The roll-to-roll sputtering process with the hybrid target of claim 6, wherein the way of forming the blocked layer comprises the following steps of screen printing, applying resist film, attaching plastic film, and photolithography.

8. The roll-to-roll sputtering process with the hybrid target of claim 6, wherein the way of removing the metal film on the unblocked area and the blocked layer comprises an etching process and a sandblasting process.

* * * * *